United States Patent
Voss et al.

[11] Patent Number: 5,972,315
[45] Date of Patent: *Oct. 26, 1999

[54] COSMETIC SKIN-CARE PRODUCT AGAINST AGEING OF THE SKIN AS AN EFFECT OF LIGHT

[75] Inventors: Eckart Voss, Leverkusen; Peter Finkel, Köln, both of Germany

[73] Assignee: Sara Lee/DE N.V., Netherlands

[*] Notice: This patent is subject to a terminal disclaimer.

[21] Appl. No.: 08/986,775

[22] Filed: Dec. 8, 1997

Related U.S. Application Data

[63] Continuation of application No. 08/408,239, Mar. 22, 1995, abandoned, which is a continuation of application No. 08/076,294, Jun. 11, 1993, abandoned.

[30] Foreign Application Priority Data

Jul. 16, 1992 [DE] Germany .............................. 42 23 463

[51] Int. Cl.$^6$ ................................ A61K 7/42; A61K 7/44
[52] U.S. Cl. .............................. 424/59; 424/60; 424/401; 514/458; 514/938; 514/946; 514/947
[58] Field of Search ................................ 424/401, 59, 60; 514/458, 844, 845, 847, 946, 938, 947

[56] References Cited

U.S. PATENT DOCUMENTS

| | | | |
|---|---|---|---|
| 4,826,828 | 5/1989 | Wilmott et al. ............................ | 514/63 |
| 4,997,649 | 3/1991 | Papaconstantin et al. ........... | 424/195.1 |
| 5,002,760 | 3/1991 | Katzev ...................................... | 424/59 |
| 5,102,654 | 4/1992 | Castrogiovanni et al. ............... | 424/61 |
| 5,118,507 | 6/1992 | Clement .................................... | 424/401 |
| 5,372,805 | 12/1994 | Finkel et al. .............................. | 424/59 |
| 5,443,840 | 8/1995 | Morancais et al. ..................... | 424/450 |
| 5,601,833 | 2/1997 | Ribier et al. ............................. | 424/401 |
| 5,614,215 | 3/1997 | Ribier et al. ............................. | 424/450 |
| 5,629,015 | 5/1997 | Ribier et al. ............................. | 424/450 |
| 5,658,575 | 8/1997 | Ribier et al. ............................. | 424/401 |
| 5,756,108 | 5/1998 | Ribier et al. ............................. | 424/401 |
| 5,834,013 | 11/1998 | Ribier et al. ............................. | 424/450 |

OTHER PUBLICATIONS

Finnen, M.J., et al., "Inhibition of Dithranol Inflammation by Free–Radical Scavengers", The Lancet, vol. 2, No. 8412, Issued Nov. 17, 1984, pp. 1129–1130.

"A Potent Elixir for Younger Looking Skin", Cosmetic & Toiletries Manufacturers & Suppliers, Issued Nov. 1991, pp. 18.

Primary Examiner—Robert H. Harrison
Attorney, Agent, or Firm—Pillsbury Madison & Sutro

[57] ABSTRACT

The present invention relates to a new cosmetic skin-care product for external use, which is based on UV-radiation-absorbing substances in combination with a free-radical scavenger system.

10 Claims, No Drawings

COSMETIC SKIN-CARE PRODUCT AGAINST AGEING OF THE SKIN AS AN EFFECT OF LIGHT

This application is a continuation of application Ser. No. 08/408,239, filed Mar. 22, 1995, now abandoned; which is a continuation of Ser. No. 08/076,294 filed Jun. 11, 1993, now abandoned.

The present invention relates to a new cosmetic skin-care product for external use, which is based on UV-radiation-absorbing substances in combination with a free-radical scavenger system.

Along with nutritive components, cosmetic skin-care products conventionally contain UV B and/or UV A filters to reduce the UV radiation which is responsible for ageing the skin. However, a large part of this radiation reaches deep layers of the skin, and damages them in a multitude of ways. The most important damaging mechanism is the formation of free radicals, which are very high-energy intermediates which, in an entirely unselective manner, attack precisely those skin constituents which are responsible for elasticity and moisture retention.

Among the most effective free-radical scavengers are the vitamin E derivatives, whose biological action is based on the antioxidant action of the compounds themselves (H. M öller et al. Parfümerie und Kosmetik, 68, 11, 688 (1987). However, the function of conventional vitamin E derivatives as free-radical scavengers in cosmetic skin-care products is limited by the insufficient and/or inhomogeneous distribution within the epidermis. Under normal conditions, for example, it is particularly the sensitive basal layer of the epidermis where only relatively low concentrations of active compound can be obtained, and even liposomes, which are currently widely employed as vehicles, provide no substantial improvement with regard to this.

A new cosmetic skin-care product against ageing of the skin as an effect of light has now been found, which contains, along with conventional bases and auxiliaries, a combination of vitamin E or derivatives thereof and 2-(dihydroxyethyl)-2-hydroxy-6,10,14-trimethyl-pentadecane, as well as, if appropriate, at least one UV filter.

2-(Dihydroxyethyl)-2-hydroxy-6,10,14-trimethyl-pentadecane is known from the literature as a hair and skin-care product, where it helps to retain the moisture of the hairs, to protect the hair against mechanical damage, to favour the penetration of panthenol and amino acids into the hair follicle, to impart new lustre to dull hair, to increase the moisture retention capacity of the skin and to keep the skin smooth and supple. (G. Erlemann et al., Seifen, Öle, Fette 117, 10, 379 (1991).

To date, nothing has been disclosed about the use of 2-(dihydroxyethyl)-2-hydroxy-6,10,14-trimethyl-pentadecane together with vitamin E and derivatives thereof. This compound causes increased penetration and/or diffusion of vitamin E, and derivatives thereof, into the, or in the, skin.

Furthermore, it has been found that the new cosmetic skin-care product according to the invention, against ageing of the skin as an effect of light, which consists of bases and auxiliaries conventionally used in cosmetics, a combination of UV filter and vitamin E or derivatives thereof, 2-(dihydroxyethyl)-2-hydroxy-6,10,14-trimethyl-pentadecane and, if appropriate, at least one UV filter, is obtained when the components are mixed with each other and the mixture is stirred and, if appropriate, subsequently homogenised. The entire preparation is preferably carried out in an evacuated apparatus to avoid the inclusion of air.

The present invention generally also relates to the new use of 2-(dihydroxyethyl)-2-hydroxy-6,10,14-trimethyl-pentadecane for increasing the penetration and/or diffusion of vitamin E, or the derivatives thereof, into the, or in the, skin, in particular in cosmetic skin-care products.

Surprisingly, the cosmetic skin-care product according to the invention shows none of the usual disadvantages compared with cosmetic formulations known from the prior art.

To optimise the use of vitamin E, a range of experiments were carried out to improve the penetration and diffusion of the substance in the epidermis, and it was demonstrated that a combination of vitamin E derivatives with 2-(dihydroxyethyl)-2-hydroxy-6,10,14-trimethyl-pentadecane results in a completely homogeneous distribution of the vitamin E derivatives over the total area of the epidermis. It was also demonstrated that the skin-care product according to the invention builds up a depot of vitamin E derivative in the skin, in particular in the deeper areas of the epidermis, which are important in the ageing processes. This is an optimum prerequisite for using a free-radical scavenger system in skin which is exposed to light.

The cosmetic skin-care product according to the invention is therefore a highly effective system for protecting the skin while having excellent cosmetic properties.

According to the invention, the customary vitamin E derivatives are preferably employed, and the vitamin E esters may be mentioned as being particularly preferred. Vitamin E linoleate and vitamin E acetate, or mixtures of these, are very particularly preferably used.

The cosmetic skin-care product according to the invention, against ageing of the skin as an effect of light, preferably contains 0.1 to 10% of vitamin E linoleate and/or vitamin E acetate and 0.1 to 10% of 2-(dihydroxyethyl)-2-hydroxy-6,10,14-trimethyl-pentadecane and, if appropriate, 0.1 to 20% of one or more UV filters, along with the bases and auxiliaries customary in skin-care products.

The cosmetic skin-care product against ageing of the skin as an effect of light particularly preferably contains 0.3 to 8% of vitamin E linoleate and/or vitamin E acetate and 0.3 to 5% of 2-(dihydroxyethyl)-2-hydroxy-6,10,14-trimethyl-pentadecane and, if appropriate, 0.3 to 10% of one or more UV filters, along with the bases and auxiliaries customary in skin-care products.

The abovementioned cosmetic skin-care products preferably contain at least one UV filter in the concentration ranges indicated.

Suitable as UV filters are preferably all UV-absorbing compounds which are mentioned in the EC positive list and which are published in the Fourteenth Guideline 92/8/EEC of the Commission, dated Feb. 18, 1992.

These filters are generally benzylidenecamphor compounds, p-aminobenzoic acid and derivatives thereof, cinnamates, benzoxazole derivatives; benzophenone derivatives and benzotriazole derivatives.

The following compounds are preferably employed as UV filters:

N-propoxylated ethyl 4-aminobenzoate (mixture of isomers) ethoxylated ethyl 4-aminobenzoate glyceryl 4-aminobenzoate 2-ethylhexyl-4-dimethylaminobenzoate 2-ethylhexyl salicyclate isopentyl 4-methoxycinnamate (mixture of isomers)

2-ethylhexyl 4-methoxycinnamate 2-hydroxy-4-methoxy-4'-methyl-benzophenone [mexenone (INN)]

2-hydroxy-4-methoxybenzophenone-5-sulphonic acid and sodium salt (sulisobenzone and sodium salt), α-(2-oxoborn-3-ylidene-toluene)-4-sulphonic acid and salts thereof 3-(4'-methylbenzylidene)-d,1-camphor 3-benzylidenecamphor 4-isopropyl-dibenzoylmethane 4-isopropylbenzyl salicyclate 1-(4-tert-butylphenyl)-3-(4-methoxyphenyl)propane-1,3-dione 2,4,6-trianilin-(p-carbo-2'-ethylhexyl-1'-oxy)-1,3,5-triazine.

The following compounds are particularly preferably used as UV filters:

2-ethoxyhexyl p-(dimethylamino)-benzoate;

2-ethylhexyl p-methoxycinnamate;

3-(4'-methylbenzylidene)-d,1-camphor;

2-hydroxy-5-methoxybenzophenone;

2-hydroxy-4-methoxybenzophenone-5-sulphonic acid;

2-phenylbenzimidazole-5-sulphonic acid.

Along with the abovementioned combination of active compounds, the cosmetic product according to the invention contains bases and auxiliaries which are conventionally employed in cosmetics, in particular stabilisers and antioxidants such as butylhydroxyanisole, butylhydroxy-toluene, EDTA salts such as magnesium sulphate, in amounts from 0.02 to 5%, inter alia.

The bases and auxiliaries additionally include solvents which are customary in cosmetics, such as water to 80%, monoalcohols, lower polyalcohols having 1 to 6 carbon atoms or mixtures of these, furthermore fatty material, such as mineral, animal, or vegetable oils such as paraffin oil, or waxes such as microwax, fatty acids, fatty alcohols, fatty acid esters such as cetylstearyl isononanoate and isopropyl palmitate, fatty alcohol ethers, oxyethylated fatty alcohols, lanolin and derivatives, as well as silicone oils in amounts from 0.5 to 50%, preferably 0.5 to 30%, particularly preferably in amounts from 5 to 30%.

If appropriate, the cosmetic skin-care product according to the invention contains emulsifiers in amounts from 0.1 to 20%, preferably in amounts from 0.2 to 10%, these emulsifiers being emulsifiers conventionally employed in cosmetics, in particular non-ionic, anionic, cationic or amphoteric compounds, for example sterols, polyol fatty acid esters and polyol fatty alcohol ethers, alkali metal salts and triethanolamine salts of fatty acids, sodium cetylstearyl sulphate, tetracylammonium halides and phospholipids. Examples of these are glycerol sorbitan fatty acid esters, polyoxyethylene fatty acid esters and alkyltetraglycol ether o-phosphoric acid esters.

0.02 to 5%, preferably 0.1 to 2%, of thickeners and gelling agents can furthermore be employed in the product according to the invention. These include polyacrylic acid derivatives, cellulose derivatives, bentonites, xanthan derivatives, alginates, guar gum and locust bean gum. Polyacrylamide and zinc stearate are examples.

The preparation according to the invention can contain other substances which are customary in cosmetics. These include humectants (0.5 to 15%), colorants, buffer substances, preservatives and perfume oils in amounts from 0.01 to 5.0%.

The following may be mentioned by way of example as humectants: lower polyalcohols such as glycerol, propylene glycol, butylene glycol, sorbitol, moreover 2-pyrrolidone-5-carboxylic acid and the sodium salt thereof, lactic acid and the salts thereof, urea, proteins and protein derivatives such as collagen, and furthermore hyaluronic acid, inter alia.

Colorants to be added to the cosmetic preparations according to the invention which may be mentioned by way of example are:

Colour C.I. 16255, colour C.I. 61570, colour C.I. 42051, colour C.I. 15985, colour C.I. 77492.

The following are preferably suitable as preservatives:

2,4-hexadienoic acid (sorbic acid and salts thereof), 4-hydroxybenzoic acid, salts and esters thereof, 3-acetyl-6-methyl-2,4(3H)-pyrandione (dehydracetic acid) and salts thereof, 1,1-methylene-bis-(3-(1-hydroxymethyl-2,4-dioximidazolidin-5-yl)-urea), imidazolindinylurea, 2-phenoxy-ethanol, benzyl alcohol.

The cosmetic skin-care product according to the invention is preferably in the form of an emulsion (cream or milk), such as oil-in-water or water-in-oil emulsions. It is generally prepared by mixing and stirring of the components, if appropriate followed by homogenisation, and if appropriate and preferably in an evacuated apparatus.

All percentages in the present text relate to percentages by weight, unless stated otherwise.

The invention is illustrated hereinafter in greater detail with the aid of the examples, without this being intended to have a restrictive character.

EXAMPLE 1a

| | Oil-in-water emulsion (skin-care cream) | | (Data in g) |
|---|---|---|---|
| I. | Polysorbate 60 | | 1.5 |
| | Sorbitan stearate | (emulsifier) | 0.9 |
| | Octyldodecanol | | 10.0 |
| | Cetearyl alcohol | (fat components) | 6.0 |
| II | Polyacrylamide | (thickener) | 0.6 |
| III. | Vitamin E linoleates | | 5.0 |
| | 2-(Dihydroxyethyl)-2-hydroxy-6,10,14-trimethyl-pentadecane | | 2.0 |
| IV. | Perfume oil | | 0.3 |
| | Preservative | | q.s.* |
| V. | Glycerol | (humectant) | 5.0 |
| | Water | to | 100.0 |

EXAMPLE 1b

Composition as in Example 1a but additionally 2.0 g of ethyl p-methoxycinnamate as UV B filter and a water content of 66.1 g.

Preparation of Examples 1a and 1b:

Mixture I is fused at 75° C., II is added to form a dispersion, and the mixture is added to solution V, which has been heated to the same temperature. The mixture is allowed to cool to 35° C. with further stirring and homogenisation, mixture III and IV are then added, the mixture is made up with water to 100 g and allowed to cool to room temperature with further stirring. The entire preparation is carried out in an evacuated apparatus to avoid the incorporation of air.

EXAMPLE 2a

| | Oil-in-water emulsion (skin-care lotion) | | (Data in g) |
|---|---|---|---|
| I. | Trilaureth-4-phosphate | (emulsifer) | 1.0 |
| | Parrafin oil, low viscosity | (fatty | 10.0 |
| | Isopropyl palmitate | acid components) | 5.0 |
| II. | Polyacrylamide | (thickener) | 0.8 |

-continued

| Oil-in-water emulsion (skin-care lotion) | | (Data in g) |
|---|---|---|
| III. Vitamin E linoleate | | 0.5 |
| 2-(Dihydroxyethyl)-2-hydroxy-6,10,14-trimethyl-pentadecane | | 0.5 |
| IV. Perfume oil | | 0.3 |
| Preservative | | q.s. |
| V. Glycerol | (humectant) | 5.0 |
| Saccharides isomerates | | 3.0 |
| Water | to | 100.0 |

EXAMPLE 2b

Composition as in Example 2a, but additionally 2.0 g of UV B filter and a water content of 71.3 g.
Preparation of Examples 2a and 2b:
Mixture I is fused at 75° C., II is added to form a dispersion, and the mixture is added to solution V, which has been heated to the same temperature. The mixture is allowed to cool to 35° C. with further stirring and homogenisation, mixture III and IV are then added, the mixture is made up with water to 100 g and allowed to cool to room temperature with further stirring. The entire preparation is carried out in an evacuated apparatus to avoid the incorporation of air.

EXAMPLE 3a

| Water-in-oil emulsion (skin-care cream) | | Data in g |
|---|---|---|
| I. Cetyl dimethicones copoliol | (emulsifier) | 5.0 |
| (and) cetyldimethicone | (and) | |
| polyglyceryl-3-oleate | (and) | |
| hexyl laurate | | |
| Isohexadecane | (fat | 8.0 |
| Capryic/caproic triglycerides | com- | 8.0 |
| Microwax | ponents) | 5.0 |
| Ethyl p-methoxycinnamate | (UV B filter) | 2.0 |
| II. Vitamine E linoleate | | 2.0 |
| 2-(Dihydroxyethyl)-2-hydroxy-6,10,14-trimethyl-pentadecane | | 1.0 |
| III Perfume oil | | 0.5 |
| Preservative | | q.s. |
| IV. Glycerol | (humectant) | 3.0 |
| Sodium chloride | (stabiliser) | 1.5 |
| Water | to | 100.0 |

EXAMPLE 3b

Composition as in Example 3a, but without UV B filter and a water content of 65.4 g.
Preparation of Examples 3a and 3b:
Mixture I is fused at 75° C., and solution IV, which has been heated to the same temperature, is added with stirring.
The mixture is cooled to 35° C. with further stirring and homogenisation, the mixture II and III are then added, and the mixture is made up to 100 g with water and allowed to cool to room temperature, with further stirring. The entire preparation is carried out in an evacuated apparatus in order to avoid the incorporation of air.

It will be understood that the specification and examples are illustrative but not limitative of the present invention and that other embodiments within the spirit and scope of the invention will suggest themselves to those skilled in the art.

What is claimed is:

1. A cosmetic vitamin E skin penetrate composition, comprising by weight:

0.3 to 10% of a vitamin E derivative selected from the group consisting of vitamin E linoleate, vitamin E acetate and mixtures thereto;

0.1 to 10% of 2-(dihydroxyethyl)-2-hydroxy-6,10,14-trimethyl-pentadecane; and at least one UV filter.

2. The composition of claim 1, wherein the vitamin E derivative is vitamin E linoleate.

3. The composition of claim 1, wherein the vitamin E derivative is vitamin E acetate.

4. The composition of claim 1, wherein said one or more UV filter is present in an amount of 0.1 to 20%.

5. The composition of claim 1, wherein said vitamin E derivative is present in an amount of 0.3–8%; said 2-(dihydroxyethyl)-2-hydroxy-6,10,14-trimethyl-pentadecane is present in an amount of 0.3 to 5% and said UV filter is present in an amount of 0.3 to 10%.

6. The composition of claim 1, wherein said composition is an oil-in-water or an water-in-oil emulsion.

7. The composition of claim 1, wherein said vitamin E derivative is present in an amount of 0.3–8%; and said UV filter is present in an amount of 0.1 to 20%.

8. The composition of claim 1, further comprising one or more cosmetic base or cosmetic auxiliary.

9. The composition of claim 7, wherein said cosmetic base or auxiliary is one or more of the following; antioxidants, solvents, mineral, animal or vegetable oils or waxes, fatty acids, fatty alcohols, fatty acid esters, fatty alcohol ethers, ethoxylated fatty alcohols, lanolin or lanolin derivatives, silicone oils, emulsifiers, thickeners, humectants, colorants, buffer substances, preservatives and perfume oils.

10. A method of increasing the penetration of vitamin E into the skin of a subject comprising applying the composition of claim 1.

* * * * *